United States Patent [19]

Boguth et al.

[11] 3,988,205
[45] Oct. 26, 1976

[54] OPTICALLY ACTIVE CYCLOHEXANE DERIVATIVES

[75] Inventors: Walter Boguth, Riehen; Hans Georg Wilhelm Leuenberger, Arlesheim; Hans Johann Mayer, Fullinsdorf; Erich Widmer, Munchenstein; Reinhard Zell, Rodersdorf, all of Switzerland

[73] Assignee: Hoffmann-La Roche Inc., Nutley, N.J.

[22] Filed: Aug. 4, 1975

[21] Appl. No.: 601,770

[30] Foreign Application Priority Data
Aug. 21, 1974 Switzerland.................. 11434/74
Nov. 1, 1974 Switzerland.................. 14674/74
July 16, 1975 Switzerland.................. 9303/75

[52] U.S. Cl............................................. 195/51 R
[51] Int. Cl.$^2$........................................ C12D 13/00
[58] Field of Search............................. 195/51 R, 2

[56] References Cited
UNITED STATES PATENTS
3,432,393  3/1969  Bellet et al..................... 195/51 R

*Primary Examiner*—Alvin E. Tanenholtz
*Attorney, Agent, or Firm*—Samuel L. Welt; Bernard S. Leon; William H. Epstein

[57] ABSTRACT

A process for fermentatively hydrogenating and reducing ketoisophorone to produce optically active [4-R,6R]-4-hydroxy-2,6,6-trimethyl-cyclohexanone useful as an intermediate in the production of optically active carotenoids and intermediates in the production of these carotenoids.

4 Claims, No Drawings

OPTICALLY ACTIVE CYCLOHEXANE DERIVATIVES

SUMMARY OF INVENTION

The process of this invention comprises a means for producing optically active cyclohexane derivatives by fermentatively hydrogenating ketoisophorone of the formula:

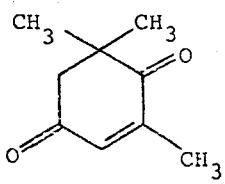

(I)

in an aqueous medium to produce [6R]-2,2,6-trimethyl-1,4-cyclohexanedione of the formula:

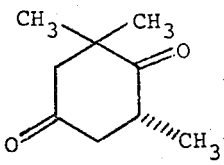

(II)

which is reduced to produce [4R,6R]-4-hydroxy-2,2,6-trimethyl-cyclohexanone of the formula:

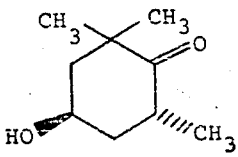

(III)

The compound of formula III can, if desired, be converted to known optically active carotenoids useful as food coloring agents.

DETAILED DESCRIPTIONS

The term lower alkanoyl designates a lower alkanoyl substituent containing from 2 to 7 carbon atoms such as acetyl, butyryl. The term lower alkyl designates both straight and branched chain saturated hydrocarbon groups containing from 1 to 7 carbon atoms such as methyl, ethyl, propyl, isopropyl, etc. The term lower alkoxy designates lower alkoxy groups containing from 1 to 7 carbon atoms such as methoxy, ethoxy, isopropoxy, etc.

The term "lower alkane" designates a saturated hydrocarbon containing from 1 to 7 carbon atoms. Therefore lower alkane carboxylic acid designates acids containing from 2 to 8 carbon atoms such as acetic acid, propionic acid, butyric acid, etc. The term lower alkane dicarboxylic acid designates alkane dicarboxylic acids containing from 3 to 9 carbon atoms.

The substituents in the structural formulae given in this specification are characterised by the notation insofar as they lie in front of the plane of the molecule and by the notation ⦀⦀⦀ insofar as they lie behind the plane of the molecule. The substituents in the structural formulae which are not stereochemically characterised in any particular manner in this specification can have either the R or S configuration. The compounds can also be present as mixtures of the R- and S-isomers.

The fermentative hydrogenation of a compound of formula I to the compound of formula II can be carried out utilizing any microorganism capable of converting ketoisophorone to [6R]-2,2,2-trimethyl-1,4-cyclohexanedione. The fermentation can be carried out either aerobically or anaerobically in an aqueous medium. Aerobic fermentation is preferred.

It is preferred that the microorganism should be cultured before use in the present fermentation. This can be carried out in a manner known per se in an aqueous medium in the presence of the usual nutrient substances, namely in the presence of a carbon source such as glucose, fructose, saccharose and/or maltose, a nitrogen source such as urea, peptone, yeast extract, meat extract, amino acids and/or ammonium salts, inorganic salts such as magnesium, sodium, potassium, calcium and/or iron salts and other growth-promoting substances such as amino acids and vitamins. It is also often expedient to use the culture medium in the present fermentation, although, as will be described hereinafter, the composition of the fermentation medium can be substantially simpler.

The fermentation of the compound of formula I to a compound of formula II can be carried out utilizing any conventional means.

This fermentation can be carried out in the absence of additives other than the ketoisophorone and the microorganism to be used. It is advantageous, however, to add a source of assimilable carbon as a microorganism nutrient substance to the aqueous medium in order to maintain the viability and the metabolic activity of the microorganism for as long as possible. The source of assimilable carbon is preferably added in an amount of from about 10 to about 100 g per liter and may be, for example, a sugar such as glucose, fructose, saccharose, maltose or the like. If desired amounts of the carbon source greater than 100 g per liter of nutrient medium can be added. However, since such large amounts do not influence the final result, no advantage is seen in utilizing over 100 g per liter of the carbon source. The addition of a nitrogen source is not necessary. However it is possible to add a source of assimilable nitrogen, preferably in an amount of about 1–50 g per liter. The source is assimilable nitrogen may be, for example, urea, peptone, yeast extract, meat extract, amino acids, ammonium salts and the like. The culture medium can also contain inorganic salts such as magnesium, sodium, potassium, calcium and/or salts, other growth-promoting substances such as amino acids, vitamins and the like.

The pH at which the fermentation is carried out is preferably within the range of from about 2 to about 10, especially from about 3 to 8, and this is generally achieved without special additives. If desired, the pH can be regulated by using buffers; for example phosphate, phthalate or tris buffer [tris-(hydroxymethyl)-aminomethane]. The temperature at which the fermentation is carried out can vary within wide limits (e.g. between 4° C and 50° C). A temperature of 15° C to 35° C, especially 25° C to 35° C, is preferred. In order to obtain optimal yields it is preferred that the ketoisophorone be present in the fermentation medium in a concentration of about 0.1–2.0% by weight, especially 0.5–1.2% by weight. After completion of the fermentative hydrogenation, fresh ketoisophorone can be added in a preferred concentration of from about 0.5–1% by weight. This procedure can be repeated several times until the microorganism becomes inactivated. In a preferred fermentation procedure using press-yeast as the microorganism, there can be fermented, with periodic educt addition, up to 10%, preferably 6–8% by weight of ketoisophorone in the same batch. The fermentation temperature in the case of this periodic educt addition is advantageously 15°–25° C.

The effective fermentation time depends on the microorganism used, but normally varies between 10 and 200 hours. In a preferred procedure in which the microorganism is press-yeast, the preferred fermentation time is 10 to 30 hours in a single educt addition. In the case of repeated educt addition, the fermentation time is appropriately longer and may amount to several weeks.

As mentioned earlier, the fermentation can be successfully carried out using any microorganism capable of converting ketoisophorone to [6R]-2,2,6-trimethyl-1,4-cyclohexanedione. The following may be mentioned as examples of representative microorganisms which can be used:

A. Eucaryotes

1. Yeasts of the genera
   Candida, e.g.:
     C. albicans;
     C. guillermondii;
     C. utilis.
   Kloeckera, e.g.:
     K. brevis.
   Rhodotorula, e.g.:
     R. rotundata.
   Saccharomyces, e.g.:
     S. carlsbergensis;
     S. cerevisiae;
     S. cer. ellipsoides.
   Torula
   Torulopsis, e.g.:
     T. apicola;
     T. rotundata.
2. Fungi of the genera
   Aspergillus, e.g.:
     A. clavatus;
     A. fischeri;
     A. flavus;
     A. fumigatus;
     A. ochraceus;
     A. wentii.
   Cunninghamella, e.g.:
     C. blakesleeana.
   Curvularia, e.g.:
     C. lunata.
   Cylindrocarpon, e.g.:
     C. radicicola.
   Fusarium, e.g.:
     F. culmorum;
     F. solani.
   Hypomyces, e.g.:
     H. rosellus.
   Mucor, e.g.:
     M. circinelloides;
     M. corymbifer;
     M. griseo-cyanus;
     M. hiemalis;
     M. parasiticus;
     M. spinosus;
     M. subtilissimus.
   Neurospora, e.g.:
     N. crassa.
   Penicillium, e.g.:
     P. brevi-compactum;
     P. digitatum;
     P. frequentans;
     P. griseofulvum;
     P. notatum;
     P. novae-zeelandiae;
     P. viride.
   Rhizopus, e.g.:
     R. arrhizus;
     R. nigricans;
     R. circinans.
   Trichothecium, e.g.:
     T. roseum.

B. Procaryotes

1. Gram-positive bacteria of the genera
   Arthrobacter (Corynebacterium), e.g.:
     A. simplex (C. simplex)
   Bacillus, e.g.:
     B. megaterium;
     B. sphaericus;
     B. subtilus.
   Lactobacillus, e.g.:
     L. casei rhamnosus;
     L. fermenti;
     L. leichmannii.
   Micrococcus, e.g.:
     M. lysodeikticus.
   Propionibacterium, e.g.:
     P. shermanii.
   Pediococcus, e.g.:
     P. cerevisiae.
   Staphylococcus, e.g.:
     S. albus;
     S. aureus.
   Streptococcus, e.g.:
     S. faecalis;
     S. lactis.
   Sarcina, e.g.:
     S. lutea.
2. Gram-negative bacteria of the genera
   Acetobacter, e.g.:
     A. aceti;
     A. suboxydans.
   Acetomonas, e.g.:
     A. melanogena;
     A. oxydans.
   Aerobacter, e.g.:
     A. aerogenea.
   Alcaligenes, e.g.:
     A. faecalis.
   Azotobacter, e.g.:
     A. agilis;
     A. indicus.
   Escherichia, e.g.:
     E. coli.
   Flavobacter, e.g.:
     F. dehydrogenans.
   Klebsiella, e.g.:
     K. pneumoniae.
   Pseudomonas, e.g.:
     P. fluorescens;
     P. saccharophila;
     P. testosteroni.

Proteus, e.g.:
 P. vulgaris.
Salmonella, e.g.:
 S. typhimurium.
Serratia, e.g.:
 S. marcescens.
Vibrio, e.g.:
 V. metschnikovii.
3. Mycelium-forming bacteria (Actinomycetes) of the genera
Actinomyces, e.g.:
 A. cellulosae.
Mycobacterium, e.g.:
 M. butyricum;
 M. phlei;
 M. rhodochrous;
 M. thamnopheos.
Nocardia, e.g.:
 N. asteroides;
 N. brasiliensis;
 N. opaca.
Streptomyces, e.g.:
 S. albus (Nocardia rangoonensis);
 S. fradiae;
 S. gelaticus;
 S. lavendulae;
 S. rimosus;
 S. venezuelae;
Proactinomyces, e.g.:
 P. restrictus;
 P. roseus.

The non-specificity of the required microorganism is exemplified in that any microbially infected soil and water samples from nature are capable of being used successfully as microorganism-providers in the fermentative hydrogenation process provided by this invention.

The fermentation is preferably carried out aerobically, preferably with stirring, shaking or by means of any aeration process. In order to control foam, the usual anti-foaming agents such as silicon oils, polyalkyleneglycol derivatives, soya-bean oil and the like can be added. Having regard to the non-specificity of the required microorganism, the fermentation has the advantage that it need not be carried out under sterile conditions.

After termination of the fermentation, the [6R]-2,2,6-trimethyl-1,4-cyclohexanedione is isolated from the fermentation broth in the usual manner. Extraction with a water-insoluble organic solvent is preferably used; for example, an aliphatic or cycloaliphatic hydrocarbon which may be chlorinated such as m-hexane, cyclohexane, methylene chloride, chloroform, or carbon tetrachloride, an aliphatic ester such as ethyl acetate, n-butyl acetate or amyl acetate or an aliphatic ether such as diethyl ether or diisopropyl ether. A preferred slvent is methylene chloride. According to a preferred isolation method, the fermented broth is filtered or centrifuged and the aqueous phase and the sediment worked up separately. The crude product obtained can be purified in the usual manner; for example by repeated recrystallisation.

The reduction of the oxo group in the 4-position of the resulting [6R]-2,2,6-trimethyl-1,4-cyclohexanedione of formula II to the hydroxy group i.e. the compound of formula III, proceeds in good yields with stereospecific selectivity, i.e. not only with retention of the oxo function in the 1-position but also with formation of the R,R-trans configuration for the two substituents in the 4- and 6-position (hydroxy or methyl). In carrying out this procedure, any conventional method of reducing an oxo group for a hydroxy group can be utilized. In accordance with one embodiment, the reduction can be carried out advantageously using an organoaluminium compound, especially a β-branched aluminium tri(lower alkyl) (e.g. triisobutylaluminium) or a corresponding halo-substituted derivative thereof (e.g. isobutylaluminium dichloride). In order to obtain optimal yields of the desired [4R,6R]-4-hydroxy-2,2,6-trimethyl-cyclohexanone of formula III, the aluminium compound and the [6R]-2,2,6-trimethyl-1,4-cyclohexanedione of formula II are to be used in approximately equimolar amounts. Other reducing agents which may be used are organic alkali metal aluminium hydrides such as sodium dihydrobis(2-methoxy-ethoxy)-aluminate and alkali metal borohydrides such as sodium borohydride. The reduction is preferably carried out in an inert organic solvent; for example, n-hexane, n-heptane, benzene, toluene, diethyl ether, tetrahydrofuran, a chlorinated hydrocarbon such as methylene chloride or chlorobenzene or mixtures of these solvents. A preferred solvent is methylene chloride and a preferred mixture consists of principally n-hexane in admixture with benzene. The reduction is preferably carried out at a temperature between about −70° C and room temperature (30° C). The reduction has the advantage that it is completed, especially when an aluminium alkyl or a halo-substituted derivative thereof is used, in a short time (generally in a few minutes at a temperature of about 0° C or above) whereafter, after neutralisation of the reduction mixture with acid, the desired [4R,6R]-4-hydroxy-2,2,6-trimethyl-cyclohexanone can be obtained by purification in the usual manner; for example, by chromatography on silicagel, aluminium oxide, dextran or the like or by extraction using a counter-current procedure.

The stereospecific reduction in accordance with another preferred embodiment of the invention can also be advantageously carried out by catalytic hydrogenation using Raney-nickel as the catalyst. However any method of catalytic hydrogenation can be utilized, in accordance with this invention. This catalytic hydrogenation is preferably carried out in an inert organic solvent, for example, a lower alkanol such as methanol or ethanol, an ether such as diethyl ether, diisopropyl ether or tetrahydrofuran or a lower aliphatic hydrocarbon such as n-hexane. A lower alkanol such as methanol containing approximately 5–20% by weight of glacial acetic acid is preferably used. The temperature at which this catalytic hydrogenation is carried out preferably lies in a range between about 0° C and about 50° C, with room temperature being preferred. After completion of the hydogen uptake, the mixture is separated from the catayst and worked up in the usual manner; for example as described earlier.

The resulting [4R,6R]-4-hydroxy-2,2,6-trimethyl-cyclohexanone of formula III hereinbefore is a key intermediate in the manufacture of optically active carotenoids; for example, for the manufacture of:
 [3R]-β-cryptoxanthin,
 [3R, 3'R]-zeaxanthin,
 [3R]-rubixanthin,
 [3R]-β-citraurin and
 [3R]-reticulataxanthin.

The aforementioned optically active carotenoids can be manufactured in a simple manner using methods which are known per se in carotenoid chemistry by linking e.g. a novel $C_{13}$, $C_{15}$ or $C_{20}$ building block, obtained by the chain-lengthening of [4R,6R]-4-hydroxy-2,2,6-trimethyl-cyclohexanone of formula III, with a condensation component corresponding to the desired product.

can be manufactured, for example, by condensing via a standard Wittig reaction a [3R]-3-hydroxy-retinyl-triarylphosphonium halide with 1,1-diethoxy-2,6-dimethyl-octa-2,4,6-trien-8-al and saponifying the acetal obtained.

[3R]-Reticulataxanthin of the formula

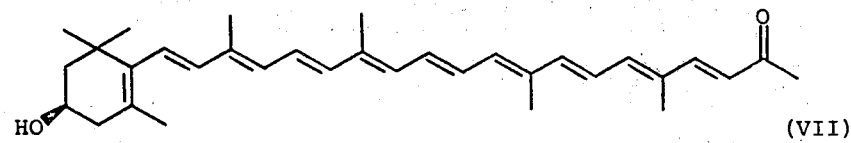

(VII)

[3R]-β-cryptoxanthin of the formula

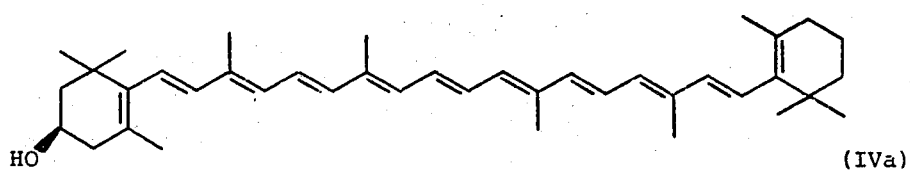

(IVa)

can be manufactured, for example by condensing a [3R]-3-hydroxy-retinyl-triarylphosphonium halide via a standard Wittig reaction with retinal. ]3,3'R]-Zeaxanthin of the formula can be manufactured, for example, by condensing [3R]-β-citraurin with acetone.

The novel $C_{20}$ building blocks required for the syntheses outlined hereinbefore, namely the [3R]-3-

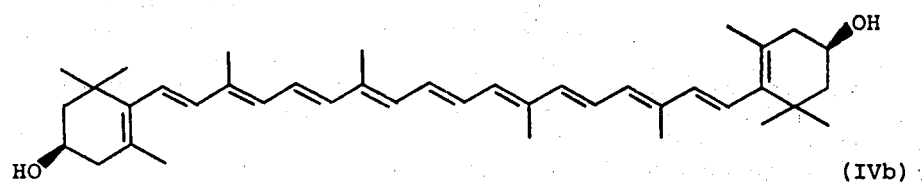

(IVb)

can be manufactured, for example, by condensing a [3R]-3-hydroxy-retinyl-triarylphosphonium halide via a standard Wittig reaction with [3R]-3-hydroxy-retinal or also by condensing a 4-[[4R]-4-hydroxy-2,6,6-trimethyl-cyclohex-1-en-1-yl]-but-3-en-2-triarylphosphonium halide via a standard Wittig reaction with 4,9-dimethyl-dodeca-2,4,6,8,10-pentaen-1,12-dial or with 4,9-dimethyl-dodeca-2,4,8,10-tetraen-6-yne-1,12-dial followed by partial hydrogenation of the resulting [3R,3'R]-15,15'-didehydrozeaxanthin.

[3R]-Rubixanthin of the formula hydroxy-retinyl-triarylphosphonium halides and [3R]-3-hydroxy-retinal, can be manufactured from [4R,6R]-4-hydroxy-2,2,6-trimethylcyclohexanone of formula III, for example by: reacting [4R,6R]-4-hydroxy-2,2,6-trimethyl-cyclohexanone of formula III with but-3-yn-2-ol;

esterifying the resulting 2-hydroxy-4-[[4R,6R]-1,4-dihydroxy-2,2,6-trimethyl-cyclohex-1-yl]-but-3-yne of the formula

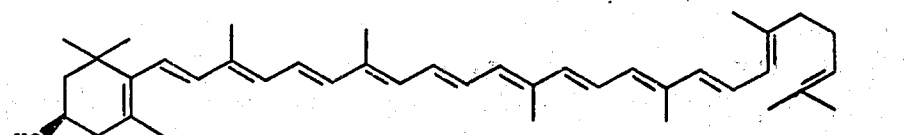

(V)

can be manufactured, for example, by condensing a [3R]-3-hydroxy-retinyl-triarylphosphonium halide via a standard Wittig reaction with γ-retinal.

[3R]-β-Citraurin of the formula

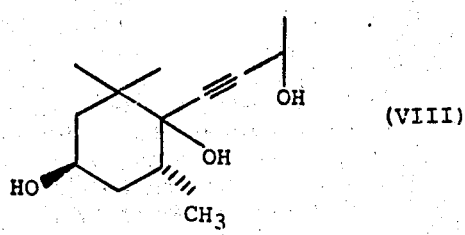

(VIII)

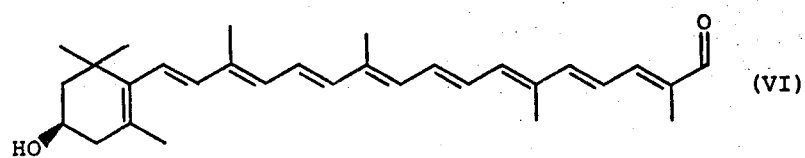

(VI)

to give 2-alkanoyloxy-4-[[4R,6R]-4-alkanoyloxy-1-hydroxy-2,2,6-trimethyl-cyclohex-1-yl]-but-3-yne of the formula

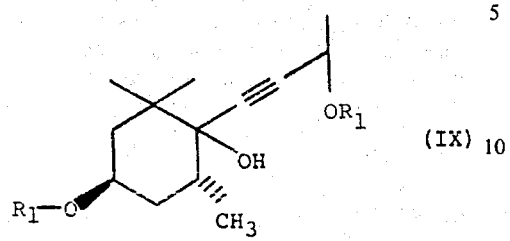

(IX)

wherein $R_1$ is lower alkanoyl,
dehydrating the compound of formula IX to give 2-alkanoyloxy-4-[[4R]-4-alkanoyloxy-2,6,6-trimethyl-cyclohex-1-en-yl]-but-3-yne of the formula

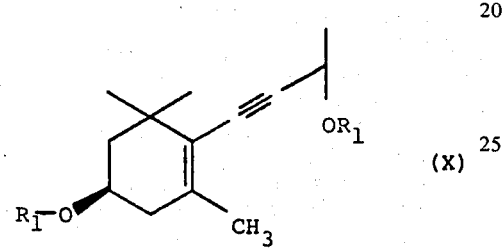

(X)

wherein $R_1$ is as above,
and hydrogenating the actylenic bond present to an ethylenic bond;

converting the resulting [3R]-3-hydroxy-β-ionol of the formula

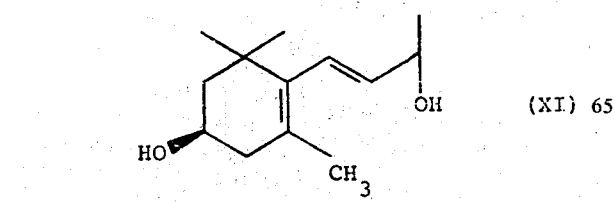

(XI)

by reaction with a triarylphosphonium halide or with a triarylphosphine in the presence of a mineral acid into a 4-[[4R]-4-hydroxy-2,6,6-trimethyl-cyclohex-1-en-1-yl]-but-3-ene-2-triarylphosphonium halide of the general formula

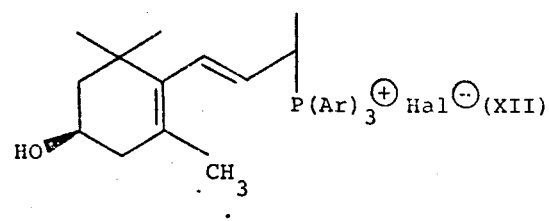

(XII)

, wherein Ar represents an aryl group such as phenyl and Hal represents a halogen atom such as a bromine atom,
and condensing this Wittig salt with 1-alkanoyloxy-3-methyl-hexa-2,4-dien-6-al to give a [3R]-3-hydroxy-retinyl ester of the formula

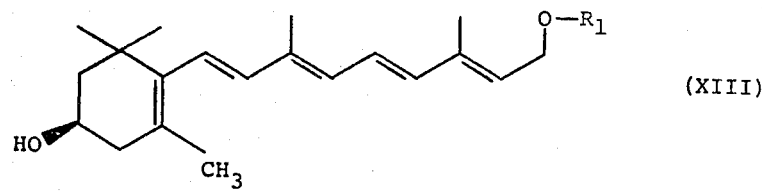

(XIII)

wherein $R_1$ is as above, and
either converting said compound of formula XIII by reaction with a triarylphosphonium halide or with a triarylphosphine in the presence of a mineral acid into a [3R]-3-hydroxy-retinyl-triarylphosphonium halide of the general formula

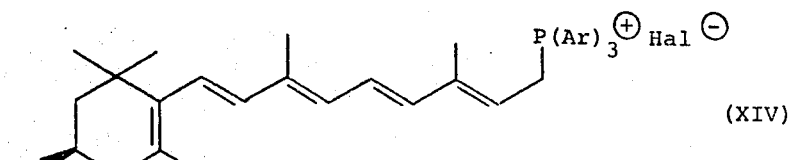

(XIV)

wherein Ar and Hal have the significance given earlier, or saponifying said compound of formula XIII to give [3R]-3-hydroxy-retinol of the formula

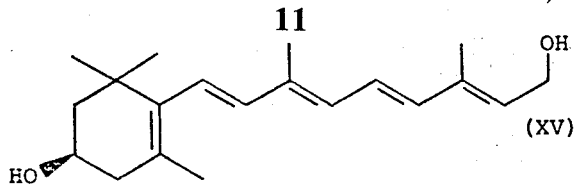

and oxidising the resulting alcohol to give [3R]-3-hydroxy-retinal of the formula

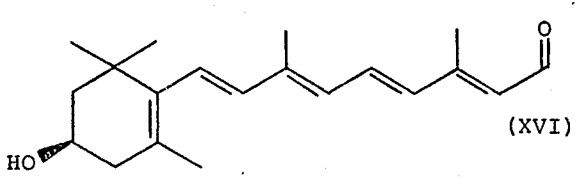

The C₁₃ building block is the above compound of formula XII. The C₁₅ building block can be prepared e.g. according to Example 13 below.

Of the optically active carotenoids mentioned earlier as capable of being manufactured from [4R,6R]-4-hydroxy-2,2,6-trimethyl-cyclohexanone of formula III, [3R]-β-cryptoxanthin and [3R,3'R]-zeaxanthin are preferred. Both of these optically active carotenoids can be manufactured in the manner previously described by converting [4R,6R]-4-hydroxy-2,2,6-trimethyl-cyclohexanone of formula III, by chain lengthening procedures which are common in carotenoid chemistry, into [3R]-β-cryptoxanthin or [3R,3'R]-zeaxanthin or derivatives thereof of the general formula

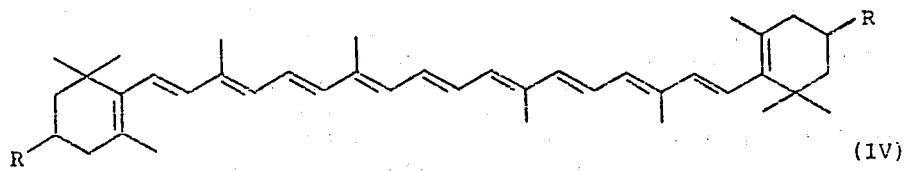

, wherein R is hydrogen, a hydroxy group having the R-configuration or an ether or ester group convertible by hydrolysis into a hydroxy group having the R-configuration, subject to the proviso that at least one of the R-substituents represents other than hydrogen,
and hydrolysing ether or ester groups present.

The aforementioned R-substituents are, according to definition, ether or ester groups convertible by hydrolysis into hydroxy.

Ether groups convertible by hydrolysis into hydroxy are, for example, the benzyloxy group or (lower alkoxy)-(lower alkoxy) groups such as the methoxymethoxy, α-methoxy-α-methyl-ethoxy or tetrahydropyranyloxy groups.

Ester groups convertible by hydrolysis into hydroxy are, for example, ester groups the acid part of which is derived from a lower alkanecarboxylic acid, a lower alkanedicarboxylic acid, an aryl-(lower alkane)carboxylic acid, phosphoric acid or carbonic acid.

The esters can be manufactured in a simple manner by condensing the hydroxy compound with a corresponding acid halide (e.g. an acid chloride or bromide), a corresponding acid anhydride (e.g. acetic anhydride) or a corresponding chloroformate (e.g. trichloroethyl chloroformate).

When R represents an ether group convertible by hydrolysis into hydroxy, this can be hydrolysed by treatment with a strong mineral acid (e.g. sulphuric acid or hydrochloric acid).

When R represents an ester group convertible by hydrolysis into hydroxy, this can be converted into a free hydroxy group not only by treatment with an acid but also by treatment with a base. Suitable acids are, in particular, mineral acids such as sulphuric and hydrochloric acid and suitable bases are, for example, aqueous alkali hydroxides, especially sodium hydroxide, or, preferably, alcoholic solutions of alkali hydroxides, especially alkali alcoholates such as sodium methylate.

[3R,3'R]-Zeaxanthin, which occupies a preferred position in the aforementioned optically active carotenoids, is identical with the natural carotenoid which is present, in particular, in maize. [3R,3'R]-Zeaxanthin is therefore extremely useful for the improving and colouring of foods, cosmetics and pharmaceutical preparations and is especially suitable for the pigmenting of egg yolks and the colouring of fat and skin of poultry.

The following examples are illustrative but not limitative of the invention. In the Examples the depositories are as follows:

ATCC = American Type Culture Collection Rockville Maryland, USA;
CBS = Central-Bureau voor Schimmelcultures Baarn — Holland;
NRRL = Northern Utilization Research and Development Division of U.S.D.A. Peoria, Illinois;
NCIB = National Collection of Industrial Bacteria Aberdeen — Scotland;
ETH = Eidgenössische Technische Hochschule Zurich — Switzerland;
PRL = Prairie Regional Laboratories Sascatoon, Canada.

In the Examples all temperatures are in °C and the ether is diethyl ether.

EXAMPLE 1

200 liters of deionised water are sterilised in a 200 liter re-circulation fermenter together with 5 kg of household sugar and then cooled to 30° C. In this sugar solution, there are first suspended 10 kg of press-yeast (baker's yeast) and subsequently dissolved 2 kg of ketoisophorone. This batch is mixed for 36 hours at a constantly maintained temperature (30° C) with a stirrer rotation rate of 800 revolutions per minute and aerated at an air flow-rate of 3200 liters/hour. The pH value amounts to 6.6 before the beginning of fermentation and 4.6 after its termination. After 6.5 hours, there are added 20 ml of polypropyleneglycol monobutyl ether in order to control the foam. Every 3 hours, a 10 ml sample is extracted with chloroform, concentrated under reduced pressure, dried, re-dissolved in 10 ml of dioxane and analysed by gas chromatography. The percentage conversion of ketoisophorone into its dihydro derivative (the dihydro derivative obtained consists of about 95–97% of the desired [6R]-2,2,6-trimethyl-1,4-cyclohexanedione) with variation of the fermentation time is recorded in Table 1:

Table 1

| Fermentation time in hours | % Conversion | Fermentation time in hours | % Conversion |
|---|---|---|---|
| 3 | 9 | 21 | 70 |
| 6 | 19 | 24 | 74 |
| 9 | 32 | 27 | 79 |
| 12 | 45 | 30 | 80 |
| 15 | 55 | 33 | 82 |
| 18 | 63 | 36 | 82 |

After discontinuing the fermentation (36 hours), the fermented broth is centrifuged. Water phase and sediment are worked up separately.

The water phase (190 liters + 5 liters of wash-water) is stirred out five times with 60 liters of methylene chloride each time. The solvent phase is separated, washed twice with 60 liters of water each time and concentrated to about 15 liters on a rotary evaporator. This concentrate is dehydrated with 1.5 kg of sodium sulphate, filtered and concentrated to dryness under reduced pressure. The residue (1755 g) is dissolved while hot in 6 liters of diisopropyl ether, decolourised with 80 g of active carbon, filtered over diatomaceous earth padding and rinsed with 1.8 liters of hot diisopropyl ether. From this solution, 2.6 liters of diisopropyl ether are distilled off at normal pressure, such that the product remains dissolved in a three-fold amount of diisopropyl ether. The product is crystallized overnight at 5° C, filtered off under suction, washed twice with 1500 ml of cold n-hexane each time and dried for 15 hours at 40° C under reduced pressure. This first crystallisation produces 1280 g of optically pure [6R]-2,2,6-trimethyl-1,4-cyclohexanedione of melting point 91°–92° C. The mother liquor contains a further 447 g of substances. The latter is taken up in the same amount of n-hexane, treated with diisopropyl ether until the solution is clear, crystallised overnight at 5° C, filtered off under suction and washed twice with a small amount of cold n-hexane. The crystallisate is dried at 40° C under reduced pressure. This second crystallisation produces 83.6 g of product with a melting point of 70°–88° C. After triple recrystallisation with the three-fold amount of diisopropyl ether, there are obtained a further 43 g of optically pure [6R]-2,2,6-trimethyl-1,4-cyclohexanedione of melting point 90.5°–91.5° C.

The sediment (wet weight ca 7 kg) is stirred out twice with 70 liters of methylene chloride each time and filtered. The filtrates are washed twice with 70 liters of water each time, concentrated to 5 liters, dried with 600 g of sodium sulphate, filtered and concentrated to dryness. The residue (82 g) is dissolved while hot in 300 ml of diisopropyl ether, decolorised with 4 g of active carbon, concentrated to 250 ml at atmospheric pressure, crystallised overnight at 5° C, filtered off under suction, washed twice with a small amount of cold n-hexane and dried at 40° C under reduced pressure. In this manner, there are obtained a further 40 g of optically pure [6R]-2,2,6-trimethyl-1,4-cyclohexanedione of melting point 90.5°–91.5° C.

The optical purity of the product is determined by NMR experiments using chiral shift reagents.

The total yield of optically pure [6R]-2,2,6-trimethyl-1,4-cyclohexanedione amounts to 1363 g. With respect to the educt (ketoisophorone) employed, this represents a relative yield of 68%.

The [6R]-2,2,6-trimethyl-1,4-cyclohexanedione shows a strongly negative Cotton effect and has a specific rotation $[\alpha]_D$ of $-265°$ (measured in methanol; $c = 0.4\%$).

EXAMPLE 2

Three soil samples taken from various places and some drops of river water are individually inoculated each into 50 ml of a sterilised culture medium of the following composition:

| | |
|---|---|
| $KH_2PO_4$ | 3.7 g/liter |
| $Na_2HPO_4$ | 7.0 g/liter |
| Yeast extract (Difco) | 10.0 g/liter |
| D (+)-Glucose monohydrate | 20.0 g/liter |

The batches are incubated on a shaking machine for 23 hours at a temperature of 30° C. Then, to each batch there are added a further 0.5 g of D(+)-glucose monohydrate (10 g/liter) as well as 0.05 g of ketoisophorone (1 g/liter) and the incubation is continued under the same conditions. After 7 days, a 10 ml sample is extracted with chloroform, concentrated under reduced pressure and dried. The residue is taken up in 1 ml of dioxane and analysed by gas chromatography. The percentage conversion of ketoisophorone into its dihydro derivative (the obtained dihydro derivative consists as in Example 1 predominantly of the desired [6R]-2,2,6-trimethyl-1,4-cyclohexanedione) is recorded in Table 2:

Table 2

| Microorganisms from: | % Conversions |
|---|---|
| Soil sample 1 | 62.1 |
| Soil sample 2 | 45.8 |
| Soil sample 3 | 71.8 |
| River water | 25.2 |

EXAMPLE 3

Two conversion Experiments A and B are carried out in clean but not sterilised small fermenters using ketoisophorone as the substrate. The fermenters are each charged with the following substances:

Table 3

| Substance | Experiment A | Experiment B |
|---|---|---|
| De-ionised water (not sterile) | 4000 ml | 3920 ml |
| Crystalline sugar | 80 g | 40 g |
| Press-yeast | 80 g | 80 g |
| Ketoisophorone | 40 g | 48 g |

The conversions are carried out under the following conditions:

Experiment A:
Temperature: 30° C
Aeration: Surface aeration, i.e. the air supply is introduced into the gas space above the broth. Air flow 240 liters/hour.
Stirrer rate: 1000 revolutions per minute
pH: 3.8–3.9
Fermentation time: 77 hours Experiment B:
Temperature: 30° C
Aeration: Through-flow aeration, i.e. the air supply is introduced into the broth below the stirring propellor. Air flow about 10 liters/hour.
Stirrer rate: 1000 revolutions per minute
pH: 3.6–4.0
Fermentation time: 142 hours After a fermentation time of 48 hours, a further 40 g of sugar and 80 g of press-yeast are added in Experiment B.

The progress of the fermentations A and B is monitored by gas chromatographic analysis of the chloroform extracts from 5 ml samples. The percentage conversion of ketoisophorone into its dihydro derivative amounts to 84% in Experiment A and 82% in Experiment B (the dihydro derivative obtained consisting as in Example 1 predominantly of the desired [6R]-2,2,6-trimethyl-1,4-cyclohexanedione).

In both batches, the fermentation product is isolated as follows:

The unfiltered broth is extracted twice with the three-fold volume of methylene chloride. The organic phase is dried over sodium sulphate and concentrated under reduced pressure. The crystalline crude product is dissolved in the five-fold volume of benzene, percolated over the three-fold amount of silica gel and again concentrated under reduced pressure. The colourless residue is dissolved while hot in the five-fold volume of n-hexane and crystallised overnight at room temperature. After removal of the solvent by suction and drying the crystals under reduced pressure at 40° C, there is obtained optically pure [6R]-2,2,6-trimethyl-1,4-cyclohexanedione.

The optical purity of the product is determined by NMR experiments using chiral shift reagents.

From Experiment A there are isolated 17.5 g and from Experiment B 27.8 g of pure [6R]-2,2,6-trimethyl-1,4-cyclohexanedione with a melting point of 90°–92° C. Accordingly, the relative net yields (product amount with respect to the educt employed) amounts to 43% and 58% respectively.

EXAMPLE 4

The conversion of ketoisophorone with semi-continuous educt addition is carried out at 20° C both in a laboratory fermenter (working volume: 5 liters) and in a large re-circulation fermenter (working volume: 160 liters). Without sterilisation, the two fermenters are charged respectively with 4.75 liters and 150 liters of deionised water in which are suspended respectively 250 g and 8 kg of press-yeast. The 5 liter fermenter is aerated by introducing an air stream of 360 liters/hour into the gas space above the broth and mixed with a baffle stirrer set at 1100 revolutions per minute. In the 160 liter fermenter, an air stream of 3200 liters/hour is introduced into the fermentation broth and the latter is mixed with the re-circulation system set at a stirring rate of 800 revolutions per minute. Ketoisophorone and sugar are added as set out in Table 4:

Table 4

| 5 liter fermenter | | | 160 liter fermenter | | |
|---|---|---|---|---|---|
| Time (hours) | Ketoisophorone | Sugar | Time (hours) | Ketoisophorone | Sugar |
| 0 | 50 g | 125 g | 0 | 1.6 kg | 4.0 kg |
| 48 | 50 g | | 46 | 0.8 kg | 0.8 kg |
| 78 | 25 g | | 70 | 0.8 kg | 0.8 kg |
| 94 | 25 g | 50 g | 94 | 0.8 kg | |
| 102 | 25 g | | 118 | 0.8 kg | |
| 126 | 25 g | | 146 | 0.8 kg | 1.6 kg |
| 149 | 25 g | | 170 | 0.8 kg | |
| 168 | 25 g | 50 g | 194 | 0.8 kg | |
| 192 | 25 g | | 218 | 0.8 kg | 1.6 kg |
| 216 | 25 g | | 242 | 0.8 kg | |
| 243 | 25 g | | 286 | 0.8 kg | |
| 267 | 25 g | 50 g | 310 | | 1.6 kg |
| 291 | 25 g | | | | |
| 335 | 25 g | | | | |
| 358 | | 50 g | | | |
| Total weight | 400 g | 325 g | Total weight | 9.6 kg | 10.4 kg |

In the 5 liter fermenter there is accordingly used a total of 80 g/liter of ketoisophorone with a sugar consumption of 65 g/liter and fermentation time of 17 days (406 hours). In the 160 litre fermenter there are used 60 g/liter of ketoisophorone with a sugar consumption of 65 g/liter and fermentation time of 16 days (384 hours). After 126 hours of fermentation time, 16 ml of propyleneglycol monobutyl ether are added in order to control the foam. The progress of the conversion reactions is monitored by regular gas chromatographic analysis of the concentrated chloroform extracts from 5 ml samples. The dihydro derivative begins to crystallise out at concentrations above 10 g/liter. After termination of the fermentation, the chloroform extracts from the 5 liter and 160 liter fermenters contain respectively 93% and 87% of the desired dihydro derivative.

The product from the 5 liter fermenter is isolated as follows:

The fermentation broth is cooled to 11° C and the resulting crystals separated using a coarse filter. A portion of the mycelium is also retained on the filter. The residue and the filtrate are extracted twice with the three-fold amount of methylene chloride. The organic phase is dried over sodium sulphate and concentrated under reduced pressure. The crystalline crude extract is recrystallised from diisopropyl ether. From the filter residue there are isolated 257.3 g of optically pure product of melting point 92°–93° C. From the filtrate and from the mother liquor there are obtained respectively a further 30.5 g and a further 15.3 g of optically pure product of melting point 91°–93° C. The optical purity can be determined by NMR examination using Eu (HFC)$_3$ as the shift reagent and by measuring the optical rotation. The total yield of [6R]-2,2,6-trimethyl-1,4-cyclohexanedione amounts to 303.1 g (75.8% yield with respect to the educt employed).

The product from the 160 litersfermenter is isolated as follows:

The broth is cooled to ca 10° C, mixed with 5 kg of diatomaceous earth and then centrifuged. The fermenter is rinsed with 20 liters of water. The sediment (crystalline product and mycelium) is extracted four times with 50 liters of methylene chloride each time. The organic phase is subsequently used as an extractant for the supernatant [first extraction: 100 liters; second and third extractions: each 50 liters], separated, washed twice with 30 liters of water each time, concentrated to ca 20 liters on a rotary evaporator, dried over sodium sulphate and concentrated to constant weight under reduced pressure. The crystalline crude extract obtained in this manner is dissolved while hot in 24 liters of diisopropyl ether, decolourised with 200 g of active carbon, filtered over diactomaceous earth padding and recrystallised overnight at 5° C. The crystallisate is filtered off under suction, washed twice with 10 liters of cold hexane (0° C) each time and dried under reduced pressure at 30° C. In this manner there are obtained 6250 g of optically pure [6R]-2,2,6-trimethyl-1,4-cyclohexanedione of melting point 91°–92° C. The mother liquor is concentrated to a volume of ca 3 liters and the substance contained therein is crystallised out overnight at 5° C. The crystallisate is in turn filtered off under suction, washed twice with 500 ml of cold hexane and dried under reduced pressure at 35° C. There are obtained a further 442 g of product with a melting point of 88°–89° C. The product is again recrystallised overnight at 5° C from 1.3 liters of diisopropyl ether, washed twice with 500 ml of cold hexane each time and dried under reduced pressure at 35° C. There thus result 399 g of optically pure [6R]-2,2,6-trimethyl-1,4-cyclohexanedione of melting point 90.5°–91.5° C. The total yield of optically pure product amounts to 6649 g (69.3% yield with respect to the substrate employed). The optical purity is again determined by NMR examination using Eu (HFC)$_3$ as the shift reagent.

EXAMPLE 5

The ability to convert ketoisophorone into its dihydro derivative is tested in 99 different microorganisms which are selected from the following groups:

A. Eucaryotes

1. Yeasts of the genera:
   Candida;
   Kloeckera;
   Rhodotorula;
   Saccharomyces;
   Torula;
   Torulopsis.
2. Fungi of the genera:
   Aspergillus;
   Cunninghamella;
   Curvularia;
   Cylindrocarpon;
   Fusarium;
   Hypomyces;
   Mucor;
   Neurospora;
   Penicillium;
   Rhizopus;
   Trichothecium.

B. Procaryotes

1. Gram-positive bacteria of the genera:
   Arthrobacter (Corynebacterium);
   Bacillus;
   Lactobacillus;
   Micrococcus;
   propionibacterium;
   Pediococcus;
   Staphylococcus;
   Streptococcus;
   Sarcina.
2. Gram-negative bacteria of the genera:
   Acetobacter;
   Acetomonas;
   Aerobacter;
   Alcaligenes;
   Azotobacter;
   Escherichia;
   Flavobacter;
   Klebsiella;
   Pseudomonas;
   Proteus;
   Salmonella;
   Serratia;
   Vibrio.
3. Mycelium-forming bacteria (Actinomycetes) of the genera:
   Actinomyces;
   Mycobacterium;
   Nocardia;
   Streptomyces;
   Proactinomyces.

Using customary microbiological techniques, the microorganisms are inoculated in 50 ml of a complex culture medium and incubated for 48–72 hours on a shaking machine at 30° C. The medium is composed as follows:

| | |
|---|---|
| KH$_2$PO$_4$ | 3.7 g/liter |
| Na$_2$HPO$_4$ | 7.0 g/liter |
| Yeast extract (Difco) | 10.0 g/liter |
| D (+)-Glucose monohydrate | 20.0 g/liter |

After 48–72 hours incubation time, a further 0.5 g of D (+)-glucose monohydrate (10 g/liter) as well as 0.05 g of ketoisophorone (1 g/liter) are added to each 50 ml batch and the incubation is continued under the same conditions for 1 week. After 1 day and after 7 days, each 10 ml of cell suspension from all batches is extracted twice with chloroform, the organic phase obtained is concentrated under reduced pressure at 40° C and dried. The residue is taken up in 1 ml of dioxane and analysed by gas chromatography. As will be seen from Table 5, all of the microorganisms are capable of converting ketoisophorone into its dihydro derivative. The dihydro derivative obtained consists as in Example 1 predominantly of the desired [6R]-2,2,6-trimethyl-1,4-cyclohexanedione, which can be isolated in the same manner as given in Example 1 or 4. In Table 5,

| | | |
|---|---|---|
| + | signifies | 0.1–10% conversion |
| ++ | signifies | 10.1–30% conversion |
| +++ | signifies | 30.1–50% conversion |
| ++++ | signifies | 50.1–70% conversion |
| +++++ | signifies | over 70% conversion | of ketoisophorone into its dihydro derivative:

Table 5

| Number | YEASTS Microorganism | | Conversion after 1 day | 7 days |
|---|---|---|---|---|
| 1 | Candida albicans | | +++ | + |
| 2 | Candida guillermondii | | +++ | + |
| 3 | Candida utilis | CBS 621 | ++ | +++++ |
| 4 | Kloeckera brevis | strain 1 | +++++ | +++++ |
| 5 | Kloeckera brevis | strain 2 | +++++ | +++++ |
| 6 | Rhodotorula sp. | | +++ | + |
| 7 | Rhodotorula rotundata | | ++ | + |
| 8 | Saccharomyces carlsbergensis | ATCC 9896 | ++++ | +++++ |
| 9 | Saccharomyces cerevisiae | strain 1 | ++++ | ++++ |
| 10 | Saccharomyces cerevisiae | strain 2 | ++ | + |
| 11 | Saccharomyces cerevisiae | strain 3 | ++ | ++ |
| 12 | Saccharomyces cer. ellipsoides | ATCC 9896 | ++++ | ++++ |
| 13 | Torula sp. | | +++ | + |
| 14 | Torulopsis apicola | PRL No. 123–64 | + | + |
| 15 | Torulopsis rotundata | NRRL 1402 | +++ | – |

| Number | FUNGI Microorganism | | Conversion after 1 day | 7 days |
|---|---|---|---|---|
| 16 | Aspergillus clavatus | | +++++ | ++ |
| 17 | Aspergillus fischeri | | +++ | +++ |
| 18 | Aspergillus flavus | | ++++ | ++++ |
| 19 | Aspergillus fumigatus Fres. | | ++ | + |
| 20 | Aspergillus ochraceus | ATCC 12 337 | ++ | ++++ |
| 21 | aspergillus sp. | ETH 2859 | ++ | + |
| 22 | Aspergillus wentii Wehmer | | +++ | ++++ |
| 23 | Cunninghamella blakesleeana (Lendner) | | ++ | ++ |
| 24 | Curvularia lunata (Wakker Boedijn) | NRRL 2380 | + | +++ |
| 25 | Cylindrocarpon radicicola | ATTCC 11011 | +++ | +++ |
| 26 | Fusarium culmorum | | ++++ | ++++ |
| 27 | Fusarium solani | ATCC 12 823 | ++ | ++++ |
| 28 | Hypomyces rosellus (Dactylium dendroides) | | + | ++ |
| 29 | Mucor circinelloides | ETH 2605 | ++++ | ++ |
| 30 | Mucor corymbifer (Absidia lichtheimi) | | +++ | ++++ |
| 31 | Mucor griseo-cyanus | | ++++ | + |
| 32 | Mucor hiemalis Wehmer | | ++++ | ++ |
| 33 | Mucor parasiticus | ATCC 6476 | ++++ | +++ |
| 34 | Mucor spinosus | ETH 2604 | ++ | + |
| 35 | Mucor subtilissimus | ETH 2607 | ++++ | + |
| 36 | Neurospora crassa | ATCC 12 623 | ++++ | +++ |
| 37 | Penicillium brevi-compactum | ETH 2733 | +++++ | ++ |
| 38 | Penicillium digitatum | NRRL 786 | + | + |
| 39 | Penicillium frequentans | CBS 591 | +++ | +++ |
| 40 | Penicillium griseofulvum | ATCC 11 885 | + | ++ |
| 41 | Penicillium notatum | CBS 832 | ++ | + |
| 42 | Penicillium novae-zeelandiae | ATCC 10 473 | ++++ | ++ |
| 43 | Penicillium viride | ETH 2603 | ++ | + |
| 44 | Rhizopus arrhizus | ATCC 11 143 | +++++ | +++ |
| 45 | Rhizopus nigricans Ehrenberg | CBS 6227 | +++++ | +++++ |
| 46 | Rhizopus circinans (Rhizopus reflexus Bain) | | ++++ | +++ |
| 47 | Rhizopus circinans v. Tiegheim | | ++++ | + |
| 48 | Trichothecium roseum | ATCC 8685 | + | + |

| Number | Gram-positive BACTERIA Microorganism | | Conversion after 1 day | 7 days |
|---|---|---|---|---|
| 49 | Arthrobacter simplex (Corynebact. simpl.)* | | + | ++ |
| 50 | Bacillus megaterium | | ++ | ++++ |
| 51 | Bacillus sphaericus | ATCC 12 300 | + | ++ |
| 52 | Bacillus subtilis | ATCC 6633 | +++ | +++++ |
| 53 | Lactobacillus casei rhamnosus | ATCC 7469 | + | + |
| 54 | Lactobacillus fermenti | ATCC 9338 | + | + |
| 55 | Lactobacillus leichmannii | ATCC 7830 | + | ++ |
| 56 | Micrococcus lysodeikticus | ATCC 4638 | + | +++++ |
| 57 | Propionibacterium shermanii | | ++ | +++++ |
| 58 | Pediococcus cerevisiae | ATCC 8042 | + | + |
| 59 | Staphylococcus albus | | + | + |
| 60 | Staphylococcus aureus | ATCC 6538 | + | + |
| 61 | Streptococcus faecalis | ATCC 9790 | + | + |
| 62 | Streptococcus lactis | | + | + |
| 63 | Sarcina lutea | ATCC 8340 | + | ++ |

| Number | Gram-negative BACTERIA Microorganism | | Conversion after 1 day | 7 days |
|---|---|---|---|---|
| 64 | Acetobacter aceti | NCIB 8621 | ++ | ++ |
| 65 | Acetobacter suboxydans | strain 1 | ++++ | ++++ |
| 66 | Acetobacter suboxydans | strain 2 NCIB 8086 | ++ | ++ |

Table 5-continued

| | | | | |
|---|---|---|---|---|
| 67 | Acetomonas melanogena | | + | ++ |
| 68 | Acetomonas oxydans | | +++++ | +++++ |
| 69 | Aerobacter aerogenea | | ++ | ++++ |
| 70 | Alcaligenes faecalis | | ++ | ++++ |
| 71 | Azotobacter agilis | ATCC 9042 | ++ | ++++ |
| 72 | Azotobacter indicus | ATCC 9540 | ++ | ++++ |
| 73 | Escherichia coli | ATCC 9637 | ++ | ++ |
| 74 | Flavobacter dehydrogenans | ATCC 13 930 | + | + |
| 75 | Klebsiella pneumoniae | | ++ | ++++ |
| 76 | Pseudomonas fluorescens | ATCC 13 430 | + | +++ |
| 77 | Pseudomones saccharophila | ATCC 15 946 | ++ | ++ |
| 78 | Pseudomonar testosteroni | ATCC 11 996 | ++ | ++++ |
| 79 | Proteus vulgaris | ATCC 9920 | +++ | +++++ |
| 80 | Salmonella typhimurium | ATCC 19 585 | ++ | ++++ |
| 81 | Serratia marcescens | | ++ | +++ |
| 82 | Vibrio metschnikovii | ATCC 7708 | ++ | ++++ |

| | ACTINOMYCETES (mycelium-forming bacteria) | | Conversion after | |
|---|---|---|---|---|
| Number | Microorganism | | 1 day | 7 days |
| 83 | Actinomyces cellulosae | | + | ++ |
| 84 | Mycobacterium butyricum | | +++ | +++ |
| 85 | Mycobacterium phlei | ATCC 354 | ++ | +++ |
| 86 | Mycobacterium phlei | | ++ | ++ |
| 87 | Mycobacterium rhodochrous | ATCC 4277 | +++ | +++ |
| 88 | Mycobacterium thamnopheos | | + | + |
| 89 | Nocardia asteroides | ETH 27 042 | ++++ | + |
| 90 | Nocardia brasiliensis | ETH 27 048 | ++ | +++++ |
| 91 | Nocardia opaca | CBS 33 161 | ++ | ++ |
| 92 | Streptomyces albus (Nocardia rangoonensis)* | | ++ | +++ |
| 93 | Streptomyces fradiae | ATCC 10 745 | + | + |
| 94 | Streptomyces gelaticus Waksman | CBS 13 120 | ++ | +++ |
| 95 | Streptomyces lavendulae | ATCC 11 924 | ++ | ++ |
| 96 | Streptomyces rimosus | ATCC 10 970 | ++ | + |
| 97 | Streptomyces venezuelae | ETH 10 210 | + | + |
| 98 | Proactinomyces restrictus Turfitt (Noc. rest.)*** | | + | + |
| 99 | Proactinomyces roseus | | ++ | ++ |

*ATCC 6946
**ATCC 6860
***CBS 15 745

EXAMPLE 6

A solution of 20 g (130 mmol) of [6R]-2,2,6-trimethyl-1,4-cyclohexanedione in 1550 ml of a mixture of n-hexane and benzene (volumetric proportion 7:3 parts by volume) is cooled in an argon atmosphere to −5° C in a four-necked flask provided with thermometer, stirrer, gassing fitment and calcium chloride tube. The gassing fitment is removed and replaced by a dropping funnel. The cooled solution is treated within about 4 minutes while stirring vigorously, with 173 ml of a 0.81-M solution of triisobutylaluminium in toluene (140 mmol) via the dropping funnel in such a manner that the internal temperature is maintained between −4° C and 0° C. The mixture is then mixed with 1085 ml of 5% by weight aqueous hydrochloric acid. Both phases are separated from one another after about 30 minutes and the aqueous phase is extracted with methylene chloride. The combined organic phases are washed to neutrality with water, dried over sodium sulphate and evaporated under reduced pressure. There are obtained 18.7 g of a yellow oil which, according to the gas chromatogram, consists of 63% of trans-4-hydroxy-6-methyl compound. After chromatographic purification of this oil an silica gel (0.06–0.2 mm) using n-hexane/diethyl ether (80/20 parts by volume) as the eluant, there are obtained 11.6 g of a product which, after recrystallisation twice from n-hexane/diisopropyl ether at −70° C, yields 10.10 g (50% by weight) of [4R,6R]-4-hydroxy-2,2,6-trimethyl-cyclohexanone as colourless crystals of melting point 49°–50° C.

The optical purity of the product is determined by NMR examination using chiral shift reagents.

Isobutylaluminium dichloride can be used instead of the triisobutylaluminium to give similar results.

EXAMPLE 7

A suspension of 30 g of Raney nickel in 200 ml of methanol in a round-bottomed flask is treated with 65 ml of glacial acetic acid while stirring. After the addition of 10 g (65 mmol) of [6R]-2,2,6-trimethyl-1,4-cyclohexanedione in 300 ml of methanol, hydrogen gas is introduced into the mixture while vigorously shaking at room temperature. After hydrogenation for 13 hours (hydrogen uptake 955 ml), the reaction product is separated from the catalyst, neutralised with sodium bicarbonate and extracted with methylene chloride. There is obtained a yellow oil which, according to the gas chromatogram, consists of 81% of trans-4-hydroxy-6-methyl compound. According to NMR examination using chiral shift reagents, the trans compound consists of 67% of [4R,6R]-4-hydroxy-2,2,6-trimethyl-cyclohexanone. The oil is worked up in the same manner as given in Example 8. There is obtained [4R,6R]-4-hydroxy-2,2,6-trimethyl-cyclohexanone, which is identical with the compound obtained according to Example 8.

EXAMPLE 8

A suspension of 30 g of Raney nickel in 150 ml of ether in a round-bottomed flask is treated with 10 g (65 mmol) of [6R]-2,2,6-trimethyl-1,4-cyclohexanedione in 150 ml of ether. Hydrogen gas is now introduced into the mixture while vigorously shaking at room temperature. After hydrogenation for 45 minutes (hydrogen uptake 1160 ml), the reaction product is separated from the catalyst and the catalyst is washed with 200 ml of diethyl ether. The ether phase is evaporated under reduced pressure. There are obtained 10 g of a yellow oil which, according to the gas chromatogram, consists of 63% by weight of trans-4-hydroxy-6-methyl compound. After chromatographic purification of this oil on silica gel (0.06–2.0 mm) with n-hexane/diethyl ether (80/20 parts by volume) as the eluant, there are obtained 4.65 g of a product which, after recrystallisation twice from n-hexane/diisopropyl ether at −70° C, yields 3.0 g (30%) of [4R,6R]-4-hydroxy-2,2,6-trimethyl-cyclohexanone as colourless crystals of melting point 49°–50° C.

The optical purity of the product is determined by NMR examination using chiral shift reagents.

EXAMPLE 9

A solution of 120 g (778 mmol) of [6R]-2,2,6-trimethyl-1,4-cyclohexanedione in 4680 ml of toluene is cooled to −40° C under an argon atmosphere in a 10 liters sulphonating flask provided with thermometer, stirrer, gassing attachment and calcium chloride tube. The suspension resulting from partial crystallisation is now treated within less than 20 seconds while continuously stirring and with the cooling bath still in place, with 1080 ml of a 20% by volume solution of triisobutyl-aluminium in toluene (1090 mmol). The internal temperature, which rises to ca −22° C during this addition, is immediately lowered to −40° C again (about 4 minutes) by the constant cooling. The mixture is left for a further 80 minutes at −40°±2° C and then treated within 30 seconds with 1334 ml of 10% by weight aqueous hydrochloric acid (4160 mmol). The two-phase mixture is stirred for a further 30 minutes without cooling and then rinsed into a 15 liter liquid-liquid extractor. The mixture is extracted in three extraction stages with a total of 2800 ml of methylene chloride. The organic phases are washed to neutrality with water, combined, dried over sodium sulphate and evaporated under reduced pressure. There are obtained 119.2 g of a yellow oil which, according to the gas chromatogram, consists of 66.7% by weight of trans-4-hydroxy-6-methyl compound [18% by weight of starting material remain in unchanged form and can be recycled depending on the isolation/purification process]. After chromatographic purification of this oil on silica gel (0.06–0.2 mmHg) using n-hexane/diethyl ether (70:30 parts by volume) as the eluant, there are obtained 79 g of product. Double recrystallisation from n-hexane/diisopropyl ether at −45° C yields 64 g (53%) of [4R,6R]-4-hydroxy-2,2,6-trimethyl-cyclohexanone as colourless crystals of melting point 49°–50° C.

EXAMPLE 10

9.8 g of [4R,6R]-4-hydroxy-2,2,6-trimethyl-cyclohexanone are dissolved in 6.8 g of isopropenyl-methyl ether. The solution is treated in the cold with 4 drops of a 1% by weight methanolic solution of p-toluenesulphonic acid, then neutralised by the addition of triethylamine and subsequently evaporated under reduced pressure. The resulting [4R,4′R]-4,4′-(isopropylidenedioxy)-bis[[6R]-2,2,6-trimethylcyclohexanone] melts at 109°–111° C after recrystallisation from hexane.

A solution of ethylmagnesium bromide in tetrahydrofuran (prepared in the usual manner from 18.2 g of magnesium, 81.8 g of ethyl bromide and 200 ml of tetrahydrofuran) is treated dropwise within 30 minutes at room temperature, with 26.6 g of but-3-yn-2-ol in 75 ml of tetrahydrofuran. The mixture is stirred under reflux conditions for 2 hours and subsequently treated dropwise with a solution of 11.1 g of [4R,4′R]-4,4′-(isopropylidenedioxy)-bis[[6R]-2,2,6-trimethylcyclohexanone] in 75 ml of tetrahydrofuran. The mixture is stirred for 12 hours under reflux conditions, subsequently acidified by the addition of 1-N aqueous sulphuric acid, then saturated with common salt and extracted with diethyl ether. The ether extract is washed to neutrality with an aqueous common salt solution, dried over sodium sulphate and evaporated under reduced pressure. The resulting oily 4-[[4R,6R]-1,4-dihydroxy-2,2,6-trimethylcyclohex-1-yl]-but-3-yn-2-ol is subsequently acetylated by treatment with acetic anhydride in the presence of pyridine. There is obtained 2-acetoxy-4-[[4R,6R]-1-hydroxy-4-acetoxy-2,2,6-trimethyl-cyclohex-1-yl]-but-3-yne as an oil, which is purified by adsorption on silica gel using n-hexane/diethyl ether (3:2 parts by volume) as the eluant.

8.6 g of 2-acetoxy-4-[[4R,6R]-1-hydroxy-4-acetoxy-2,2,6-trimethyl-cyclohex-1-yl]-but-3-yne are dissolved in a mixture of 53.5 ml of pyridine and 22 ml of phosphorous oxychloride and heated to 100° C for 18 hours. The mixture is then cooled and introduced into ice/water. The mixture is extracted with diethyl ether and the ether extract is washed to neutrality with water and 1-N aqueous sulphuric acid, dried over sodium sulphate and evaporated under reduced pressure. The resulting oily 2-acetoxy-4-[[4R]-4-acetoxy-2,6,6-trimethyl-cyclohex-1-en-1-yl]-but-3-yne is purified by adsorption on silica gel using hexane/diethyl ether (4:1 parts by volume) as the eluant.

4.0 g of 2-acetoxy-4-[[4R]-4-acetoxy-2,6,6-trimethyl-cyclohex-1-en-1-yl]-but-3-yne are dissolved in 50 ml of absolute tetrahydrofuran. The solution is added dropwise to a suspension of 2.4 g of lithiumaluminium hydride in 180 ml of tetrahydrofuran while stirring at room temperature and the mixture obtained is heated under reflux conditions for 12 hours. The mixture is cooled, treated successively with aqueous ether and an aqueous ammonium chloride solution, then saturated with common salt and thoroughly extracted with diethyl ether. The ether extract is washed to neutrality, dried and evaporated. The resulting oily 4-[[4R]-4-hydroxy-2,6,6-trimethyl-cyclohex-1-en-1-yl]-but-3-en-2-ol [[3R]-3-hydroxy-β-ionol] is purified by adsorption on silica gel using hexane/diethyl ether (1:1 parts by volume) as the eluant.

2.1 g of [3R]-3-hydroxy-β-ionol are dissolved in 50 ml of absolute methanol. After the addition of 3.43 g of triphenylphosphine hydrobromide, the solution is stirred at room temperature for 12 hours. The solvent is subsequently evaporated under reduced pressure. The residue is dissolved in 80% by weight aqueous isopropanol and shaken out twice with hexane. The isopropanol phase is evaporated under reduced pressure. The residue is dissolved in methylene chloride, dried over sodium sulphate and evaporated under reduced pressure. The remaining 4-[[4R]-4-hydroxy-2,6,6-trimethyl-cyclohex-1-en-1-yl]-but-3-ene-2-triphenylphosphonium bromide is further reacted as follows:

16.05 g of 4-[[4R]-4-hydroxy-2,6,6-trimethyl-cyclohex-1-en-1-yl]-but-3-ene-2-triphenylphosphonium bromide and 5.39 g of 6-acetoxy-4-methyl-hexa-2,4-dien-1-al are dissolved in 100 ml of isopropanol. The solution is treated dropwise while stirring at −35° C with a solution of 2.09 g of 86% potassium hydroxide in 1.5 ml of water. In so doing, the internal temperature rises to −20° C. The mixture is subsequently diluted with 100 ml of cold low-boiling petroleum ether and introduced into a mixture of 100 ml of low-boiling petroleum ether and 100 ml of ice-water. The petroleum ether phase which separates is thoroughly washed with a total of 120 ml of methanol/water (80:20 parts by volume), then dried over sodium sulphate and evaporated under reduced pressure. The resulting [3R]-3-hydroxy-retinyl acetate, which consists of about 73% 9-cis- and about 27% all-trans-[3R]-3-hydroxy-retinyl acetate, can be isomerised, for example, according to one of the following methods a) or b):

a. 3 g of the 9-cis/all-trans-[3R]-3-hydroxy-retinyl acetate isomer mixture are dissolved in 15 ml of acetonitrile. After the addition of 6 g of palladium oxide/-barium sulphate catalyst (the carrier contains 0.5% by weight palladium), the mixture is heated at 70° C for 1 hour while stirring. After cooling, the catalyst is filtered off and the filtrate evaporated in vacuo. The resulting isomer mixture consists of about 74% by weight of all-trans- and about 26% by weight 9-cis-[3R]-3-hydroxy-retinyl acetate.

b. 3.2 g of the 9-cis/all-trans-[3R]-3-hydroxy-retinyl acetate isomer mixture are dissolved in 6.5 ml of acetonitrile. After the addition of 30 mg of $Pd(C_6H_5CN)_2$ $Cl_2$ and 0.03 ml of triethylamine, the mixture is stirred at 65° C for 1 hour. After cooling, the mixture is diluted with 10 ml of water and extracted with diethyl ether. The ether extract is washed with water, dried and evaporated. The resulting isomer mixture consists of about 78% by weight all-trans- and about 22% by weight 9cis-[3R]-3-hydroxy-retinyl acetate.

The isomer mixture obtained according to method a) or b) can be separated further by crystallisation in the normal manner in order to increase the all-trans portion.

The [3R]-3-hydroxy-retinyl acetate prepared in the foregoing can be used in the manufacture of [3R,3′R]-zeaxanthin; for example according to the following method:

5 g of [3R]-3-hydroxy-retinyl acetate are dissolved in 16.5 ml of ethanol. The solution is treated dropwise at 40° C within 15 minutes with a solution of about 1.85 g of sodium hydroxide in 7.5 ml of water. The mixture is stirred for 30 minutes at 40° C, then cooled to 10° C and extracted with 20 ml of low-boiling petroleum ether. The extract is washed to neutrality with ice/water, dried and evaporated. There is obtained [3R]-3-hydroxy-retinol. 5 g of [3R]-3-hydroxy-retinol are dissolved in 50 ml of methylene chloride. After the addition of 30 g of manganese dioxide, the solution is stirred at room temperature for 24 hours. The unconsumed manganese dioxide is filtered off and rinsed with 30 ml of methylene chloride. The washings are combined with the filtrate and evaporated under reduced pressure. The residue is dissolved in 15 ml of low-boiling petroleum ether with warming. The solution is slowly cooled to −40° C. The precipitated [3R]-3-hydroxy-retinal is filtered off, washed with cold petroleum ether and dried in vacuo at room temperature. The aldehyde can be condensed without further purification with [3R]-3-hydroxy-retinyl-triphenylphosphonium bromide to give [3R,3′R]-zeaxanthin:

3.78 g of [3R]-3-hydroxy-retinyl acetate are dissolved in 10 ml of absolute methanol. After the addition of 4.15 g of triphenylphosphine hydrobromide, the solution is stirred for 12 hours at room temperature. The resulting solution of [3R]-3-hydroxy-retinyl-triphenylphosphonium bromide is diluted with 50 ml of chloroform. The solution is treated dropwise at 0°–5° C simultaneously with a solution of 0.55 g of sodium in 5.5 ml of methanol and a solution of 3.0 g of [3R]-3-hydroxy-retinal in 10 ml of chloroform. The mixture is subsequently stirred for 1 hour at room temperature, then treated with 0.57 ml of glacial acetic acid and washed twice with 50 ml each time of a 5% by weight aqueous sodium bicarbonate solution. The washings are shaken out twice with 10 ml of chloroform each time. The chloroform extracts are combined with the original chloroform solution, dried over sodium sulphate and evaporated under reduced pressure, the chloroform being successively replaced by methanol. The solvent is subsequently evaporated down to ca 50 ml. After the addition of 2.5 ml of water, the concentrate is cooled to −20° C. The precipitated [3R,3′R]-zeaxanthin is recrystallised from methylene chloride/-pentane; melting point 201°–203° C.

EXAMPLE 11

1.605 g of 4-[[4R]-4-hydroxy-2,6,6-trimethylcyclohex-1-en-1-yl]-but-3-ene-2-triphenylphosphonium bromide obtained according to Example 10 are dissolved in 10 ml of isopropanol and introduced at room temperature into a solution of 214 mg of 4,9-dimethyl-dodeca-2,4,8,10-tetraen-6-yne-1,12-dial [$C_{14}$–aldehyde] in 10 ml of methylene chloride with stirring. The resulting homogeneous solution is treated with 0.336 ml of a 50% by weight aqueous potassium hydroxide solution. The initially weakly yellow solution turns dark red after 2 to 3 minutes. The solution is stirred for a further 90 minutes at room temperature, then thoroughly extracted with methylene chloride. The combined methylene chloride extracts are washed to neutrality with water, dried over sodium sulphate and evaporated under reduced pressure. There is obtained crude cis/trans-[3R,3′R]-15,15′-didehydro-zeaxanthin which is brought to crystallisation by trituration with 3 ml of methanol in the cold, filtered off, dried and then subjected to the following isomerisation:

468 mg of cis/trans-[3R,3′R]-15,15′-didehydro-zeaxanthin are dissolved in 18 ml of acetonitrile. The solution is treated with 936 mg of a palladium oxide/-barium sulphate catalyst containing 0.5% by weight palladium, stirred for 12 hours at 70° C and subsequently cooled to room temperature. The catalyst is separated and repeatedly washed with a total of 60 ml of methylene chloride. The washings are combined with methanol and evaporated under reduced pressure. There is obtained crystalline all-trans-[3R,3′R]-15,15′-didehydro-zeaxanthin which melts at -didehydro-zeaxanthin −210° C after recrystallisation from methylene chloride and hexane.

426 mg of palladium/calcium carbonate partially inactivated catalyst are suspended in 34 ml of absolute toluene and, after the addition of 46 ml of absolute ethyl acetate and 0.0125 ml of quinoline, pre-hydrogenated. After termination of the hydrogen uptake, the catalyst mixture is treated with 213 mg of all-trans-[3R,3′R]-15,15′-didehydro-zeaxanthin and hydrogenated further at atmospheric pressure and room temperature until uptake of 8.43 ml of hydrogen. The catalyst is filtered off and washed with ethyl acetate. The washings are combined with the filtrate, washed 3 times with 2 ml of 0.1-N aqueous sulphuric acid each time and then with water, dried over sodium sulphate and evaporated under reduced pressure.

There is obtained partly oily [3R,3′R]-15-cis-zeaxanthin which is suspended in 15 ml of heptane and isomerised at 100°–110° C for 3.5 hours. All-trans-[3R,3′R]-zeaxanthin is precipitated crystalline in the cold; melting point 208.5°–209.5° C after recrystallisation from methylene chloride/methanol.

EXAMPLE 12

If in the procedure described in Example 2, the 4,9-dimethyl-dodeca-2,4,8,10-tetraen-6-yne-1,12-dial is replaced by 4,9-dimethyl-dodeca-2,4,6,8,10-pentaene-1,2-dial, then after condensation with 4-[[4R]-4-hydroxy-2,6,6-trimethyl-cyclohex-1-en-1-yl]-but-3-ene-2-triphenylphosphonium bromide and subsequent isomerisation of the resulting cis/trans-[3R,3′R]-zeaxanthin, there is obtained directly all-trans-[3R,3′R]-zeaxanthin; melting point 208°–209° C after recrystallisation from methylene chloride/methanol.

EXAMPLE 13

20 g of [3R]-3-hydroxy-β-ionol and 30 g of 2,3-dichloro-5,6-dicyano-benzoquinone are dissolved in 400 ml of absolute dioxan. The solvent is heated for 1½ hours at 50°–55° C. The solution is subsequently cooled to 0° C and the precipitated 2,3-dichloro-5,6-cyanobenzohydroquinone is filtered off. The filtrate is evaporated at 50° C under reduced pressure. The residue is dissolved in 250 ml of diethyl ether and extracted with a solution of 50 g of sodium dithionite in 250 ml of water. The ethereal phase is subsequently washed neutral with saturated aqueous sodium chloride solution, 1 N aqueous sodium hydroxide solution and again with saturated aqueous sodium chloride solution, dried over sodium sulfate and evaporated to dryness. The residual [3R]-3-hydroxy-β-ionone can be purified by adsorption on silica gel (elution with diethyl ether) and is further reacted as follows:

To a solution of sodium acetylide in liquid ammonia (prepared from 60 ml of liquid ammonia, 2.68 g of sodium and acetylene in usual manner) there are first added 6.0 ml of absolute ether and then dropwise with stirring a solution of 6.65 g of [3R]-3-hydroxy-β-ionone in 12 ml of ether. The reaction mixture is transferred into a previously cooled autoclave and shaken for 16 hours at room temperature. The autoclave is subsequently cooled to −50° C, opened and freed from liquid ammonia under simultaneous dropwise addition of n-hexane by evaporation. Thereafter 100 g of ice and 20 g of glacial acetic acid are added to the reaction mixture, and the n-hexane phase is washed with water, 5 N aqueous sodium hydrogen carbonate solution and again with water, dried over sodium sulphate and evaporated under reduced pressure. The residual [3R]-3-hydroxy-ethynyl-β-ionol is reacted further as follows:

12 g of [3R]-3-hydroxy-ethynyl-β-ionol are dissolved in 30 ml of n-hexane. The solution is hydrogenated after the addition of 300 mg of Lindlar catalyst, 180 mg of 2-dimethylamino-ethanol and 3 mg of 1,2-bis-(2-hydroxyethylthio)ethane with stirring at 20° C. After terminated hydrogenation the catalyst is filtered off and the solvent is evaporated under reduced pressure. The residual [3R]-3-hydroxy-vinyl-β-ionol can be purified by absorption on aluminium oxide (activity grade III; eluent: diethyl ether).

The [3R]-3-hydroxy-vinyl-β-ionol can also be prepared as follows:

A solution of 22.7 g. of [3R]-hydroxy-β-ionone in 150 ml of absolute toluene is added dropwise to a solution of 28.4 g of vinyl magnesium chloride in 114 ml of absolute tetrahydrofuran and 200 ml of absolute toluene. The reaction mixture is subsequently stirred for 1 hour at room temperature, then cooled to 0°–5° C, treated with 0.6 N aqueous ammonium hydroxide solution and saturated aqueous ammonium chloride solution and extracted with diethyl ether. The ether extract is washed neutral with saturated aqueous sodium chloride solution, dried and evaporated to dryness. The residual, oily [3R]-3-hydroxy-vinyl-β-ionol can be purified by absorption on aluminium oxide (activity grade IV; eluent : ether) and is reacted further as follows:

15.4 g of [3R]-3-hydroxy-vinyl-β-ionol are dissolved in 300 ml of absolute methanol. After the addition of 17.1 g of triphenyl phosphine, 26 mg of 2,6-di-(t-butyl)-p-cresol and 8.5 ml of 25% aqueous hydrochloric acid the solution is stirred for 18 hours at room temperature. The solvent is subsequently evaporated off under reduced pressure at 40° C and the residue is crystallized from hot acetone. The precipitated [3R]-3-hydroxy-β-ionylidine-ethyl-triphenyl-phosphonium chloride melts after recrystallization from methylene chloride/acetone/ethyl acetate at 211°–212° C. $[\alpha]_D^{25} = -57.2°$ ($c = 1$ in chloroform).

1.291 g of [3R]-3-hydroxy-β-ionylidene-ethyl-triphenyl-phosphonium chloride and 162 mg of 2,7-dimethyl-octa-2,6-dien-4-yn-1,10-dial ($C_{10}$-dialdehyde) are dissolved in 20 ml of methylene chloride. To the resulting homogenous solution 0.364 ml of 38% by weight aqueous potassium hydroxide solution are added at −10° to −14° C with stirring. The reaction mixture is stirred for 1 hour at −10° to −14° C and subsequently diluted with methylene chloride. The methylene chloride phase is washed neutral with water, dried over sodium sulphate and evaporated under reduced pressure. The residual, raw cis/trans-[3R,3′R]-15,15′-didehydrozeaxanthine is brought to crystallization by trituration with 6 ml of warm 90% aqueous methanol. The crystal suspension obtained is cooled to −18° C, the [3R,3′R]-15,15′didehydrozeaxanthin filtered off, dried and subsequently isomerized as follows:

477 mg of cis/trans [3R,3′R]-15,15′-didehydrozeaxanthin are dispersed in 5 ml n-heptane, treated with 5 drops of a 0.1% solution of iodine in chloroform and heated for 18 hours at 90° C with stirring. Subsequently the n-heptane is evaporated off under reduced pressure. The residual all-trans-[3R,3′R]-15,15′-didehydrozeaxanthin melts after recrystallization from methylene chloride/n-hexane at 210°–212° C.

The all-trans-[3R,3′R]-15,15′-didehydrozeaxanthin can be converted into all-trans [3R,3′R]-zeaxanthin in accordance with Example 11.

EXAMPLE 14

If in the procedure according to Example 13 the 2,7-dimethyl-octa-2,6-dien-4-yn-1,10-dial is replaced by 2,7-dimethyl-2,4,6-trien-1,10-dial, one obtains after condensation with [3R]-3-hydroxy-β-ionylidene-ethyl-triphenyl-phosphonium chloride and after isomerization of the cis/trans-[3R,3′R]-zeaxanthin which after recrystallization from methylene chloride/n-hexane melts at 208°–209° C.

EXAMPLE 15

The [3R]-3-hydroxy-β-ionylidene-ethyl-triphenyl-phosphonium chloride used in Examples 13 and 14 can be replaced by [3R]-3-hydroxy-β-ionylidene-ethyltriphenyl-phosphonium bromide which can be prepared as follows:

1.6 g of [3R]-3-hydroxy-vinyl-β-ionol are dissolved in 30 ml of absolute methanol. After the addition of 2.33 g of triphenylphosphine hydrobromide the solution is stirred for 18 hours at room temperature. The solvent is subsequently evaporated off under reduced pressure and the residue crystallized from hot acetone. The [3R]-3-hydroxy-β-ionylidene-ethyl-triphenyl-phosphonium bromide obtained melts after recrystallization from acetone at 186°–187° C. $[\alpha]_D^{25} = -55.1°$ ($c = 1$ in chloroform).

EXAMPLE 16

5.16 g of [3R]-3-hydroxy-β-ionylidene-ethyl-triphenyl-phosphonium chloride and 1.49 g of γ-acetoxytiglic aldehyde are dissolved in 120 ml of methylene chloride. To this solution there is added dropwise a solution of 1.30 g of 86% potassium hydroxide in 1.65 ml of water at −35° C with stirring. The reaction mixture is stirred for 1 hour at −35° C and subsequently diluted with cold methylene chloride. The methylene chloride phase is washed neutral with cold saturated aqueous sodium chloride solution, dried and evaporated under reduced pressure. The residue is dissolved in n-hexane and extracted with 60% aqueous methanol. The hexane phase is dried and evaporated under reduced pressure. The residual [3R]-3-hydroxy-retinyl acetate (which consists of about 46% all-trans- and about 48% 11-cis-[3R]-3-hydroxy-retinyl acetate) or the corresponding [3R]-3-acetoxy-retinyl acetate obtained therefrom by reaction with acetic anhydride in pyridine can be isomerized according to Example 10 in order to increase the all-trans portion of the product. The all-trans product obtained can subsequently be converted into [3R,3′R]-zeaxanthin according to Example 10. The saponification of the 3-acetoxy group is carried out on the [3R,3′R]-O-acetyl-zeaxanthin obtained by stirring with 1 N aqueous sodium hydroxide solution and methylene chloride at 50°–60° C.

We claim:

1. A process for producing optically active cyclohexane derivative of the formula

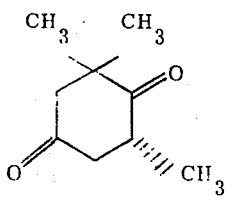

comprising subjecting a compound of the formula

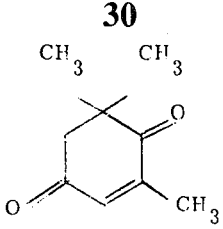

to fermentation in an aqueous medium wherein the fermentation is carried out utilizing a microorganism capable of converting ketoisophorone to a [6R]-2,2,6-trimethyl-1,4-cyclohexanedione.

2. The process of claim 1 wherein the fermentation is carried out aerobically at a pH of from about 2 to about 10.

3. The process of claim 2 wherein the fermentation is carried out at a temperature of from 4° to 50° C.

4. The process of claim 3 wherein said microorganism is selected from the group consisting of
Candida;
Kloeckera;
Rhodotorcula;
Saccharomyces;
Torula;
Torulopsis;
Aspergillus;
Cunninghamella;
Curvularia;
Cylindrocarpon;
Fusarium;
Hypomyces;
Mucor;
Neurospora;
Penicillium;
Rhizopus;
Trichothecium;
Arthrobacter;
Bacillus;
Lactobacillus;
Micrococcus;
Propionibacterium;
Pediococcus;
Staphylococcus;
Streptococcus;
Sarcina;
Acetobacter;
Acetomonas;
Aerobacter;
Alcaligenes;
Azotobacter;
Escherichia;
Flavobacter;
Klebsiella;
Pseudomonas;
Proteus;
salmonella;
Serratia;
Vibrio;
Actinomyces;
Mycobacterium;
Nocardia;
Streptomyces and
Proactinomyces.

* * * * *